(12) United States Patent
Connor

(10) Patent No.: US 10,839,202 B2
(45) Date of Patent: Nov. 17, 2020

(54) MOTION RECOGNITION CLOTHING WITH FLEXIBLE OPTICAL SENSORS

(71) Applicant: Robert A. Connor, St. Paul, MN (US)

(72) Inventor: Robert A. Connor, St. Paul, MN (US)

(73) Assignee: Medibotics, St. Paul, MN (US)

( * ) Notice: Subject to any disclaimer, the term of this patent is extended or adjusted under 35 U.S.C. 154(b) by 0 days.

(21) Appl. No.: 16/543,056

(22) Filed: Aug. 16, 2019

(65) Prior Publication Data

US 2019/0370534 A1 Dec. 5, 2019

Related U.S. Application Data

(63) Continuation-in-part of application No. 16/010,448, filed on Jun. 16, 2018, now Pat. No. 10,602,965, and a continuation-in-part of application No. 15/702,081, filed on Sep. 12, 2017, now Pat. No. 10,716,510, and a continuation-in-part of application No. 15/227,254, filed on Aug. 3, 2016, now Pat. No. 10,321,873, said application No. 15/702,081 is a continuation-in-part of application No. 14/795,373, filed on Jul. 9, 2015, now abandoned, and a continuation-in-part of application No. 15/227,254, filed on Aug. 3, 2016, now Pat. No. 10,321,873, and a continuation-in-part of application No. 14/736,652, filed on Jun. 11, 2015, now abandoned, and a continuation-in-part of application No. 14/664,832, filed on Mar. 21, 2015, now Pat. No. 9,582,072, and a continuation-in-part of application No. 15/130,995, filed on Apr. 17, 2016, now Pat. No. 9,891,718, and a continuation-in-part of application No. 15/079,447, filed on Mar. 24, 2016, now Pat. No. 10,234,934, said application No. 15/079,447 is a continuation of application No. 14/664,832, filed on Mar. 21, 2015, now Pat. No. 9,582,072, and a continuation-in-part of application No. 14/463,741, filed on Aug. 20, 2014, now Pat. No. 9,588,582, said application No. 14/795,373 is a continuation-in-part of application No. 14/736,652, filed on Jun. 11, 2015, now abandoned, and a continuation-in-part of application No. 14/664,832, filed on Mar. 21, 2015, now Pat. No. 9,582,072, and a continuation-in-part of application No. 14/463,741, filed on Aug. 20, 2014, now Pat. No. 9,588,582, which is a continuation of application No. 62/150,866, filed on Apr. 22, 2015.

(60) Provisional application No. 62/727,798, filed on Sep. 6, 2018, provisional application No. 62/683,237, filed on Jun. 11, 2018, provisional application No. 62/538,793, filed on Jul. 30, 2017, provisional application No. 62/449,735, provisional application No. 62/357,957, filed on Jul. 2, 2016, provisional application No. 62/150,886, filed on Apr. 22, 2015, provisional application No. 62/187,806, filed on Jul. 2, 2015, provisional application No. 62/182,473, filed on Jun. 20, 2015, provisional application No. 62/086,053, filed on Dec. 1, 2014, provisional application No. 62/065,032, filed on Oct. 17, 2014, provisional application No. 62/100,217, filed on Jan. 6, 2015, provisional application No. 62/104,747, filed on Jun. 20, 2014, provisional application No. 61/976,650, filed on Apr. 8, 2014, provisional application No. 61/878,893, filed on Sep. 17, 2013.

(51) Int. Cl.
| | |
|---|---|
| *G06K 9/00* | (2006.01) |
| *A61B 5/11* | (2006.01) |
| *A61B 5/00* | (2006.01) |
| *G01D 5/353* | (2006.01) |

(52) U.S. Cl.
CPC ............ *G06K 9/00342* (2013.01); *A61B 5/11* (2013.01); *A61B 5/6805* (2013.01); *G01D 5/35312* (2013.01); *G01D 5/35316* (2013.01); *A61B 5/4528* (2013.01)

(58) Field of Classification Search
CPC .. G06K 9/00342; G06K 9/00348; A61B 5/11; A61B 5/6805; A61B 5/4528; A61B 5/1113; A61B 5/1114; A61B 5/1118; A61B 5/112; A61B 5/1121; A61B 5/4585; G01D 5/35312; G01D 5/35316; G01D 5/235; G01D 5/28
USPC ............................ 73/865.4, 800; 601/33–36; 356/138–155, 614–624; 33/501, 511, 33/512, 534
See application file for complete search history.

(56) References Cited

U.S. PATENT DOCUMENTS

| | | | |
|---|---|---|---|
| 7,664,347 B2 | 2/2010 | Childers et al. | |
| 9,562,826 B2 | 2/2017 | Handerek | |
| 9,743,860 B2 | 8/2017 | Keesling | |
| 9,759,633 B2 | 9/2017 | Handerek | |
| 10,488,916 B2 * | 11/2019 | Hahami | A61B 5/6805 |
| 2011/0113852 A1 * | 5/2011 | Prisco | G01B 11/18 73/1.15 |

(Continued)

OTHER PUBLICATIONS (Wang et al., 2018), "Review of Optical Fiber Bending/Curvature Sensor," Measurement, 2018, 130.

(Continued)

*Primary Examiner* — Robert R Raevis

(57) ABSTRACT

This invention discloses optical strain, stretch, and/or bend sensors which can provide precise and consistent measurement of human motion, posture, and gestures without the locational limitations of camera-based motion capture, the point-estimate limitations of inertial-based motion capture, or the variability of electrically-conductive strain, stretch, and/or bend sensors.

1 Claim, No Drawings

(56) References Cited

U.S. PATENT DOCUMENTS

| | | | |
|---|---|---|---|
| 2012/0157263 A1* | 6/2012 | Sivak | G06F 3/014 482/4 |
| 2015/0359455 A1 | 12/2015 | Hahami et al. | |
| 2015/0370320 A1* | 12/2015 | Connor | A61B 5/1126 345/173 |
| 2017/0350733 A1 | 12/2017 | Salomonsson | |
| 2019/0029759 A1* | 1/2019 | McDonell | G02B 6/02042 |

OTHER PUBLICATIONS (Wang et al., 2018), "Self-Organized Structures of Soliton Molecules in 2-m Fiber Laser Based on Mos2 Saturable Absorber," IEEE Photonics Technology Letters, Jul. 1, 2018, vol. 30.

(Xu et al., 2017), "Dual-Layer Orthogonal Fiber Bragg Grating Mesh Based Soft Sensor for 3-Dimensional Shape Sensing," Optics Express, 2017, vol. 25, Issue 20, 24727-24734.

(Yoon, 2018), "Elastomer Thin-Film Pressure Sensor Based on Embedded Photonic Tunnel-Junction Arrays," Optics Letters, 2018, vol. 43, Issue 16, 3953-3956.

(Zhao, 2017), "Fabrication, Sensation and Control of Fluidic Elastomer Actuators and Their Application Towards Hand Orthotics and Prosthetics," Cornell Dissertation, 2017, Ph.

(Chen, 2010), "Highly Sensitive Bend Sensor Based on Bragg Grating in Eccentric Core Polymer Fiber," IEEE Photonics Technology Letters, vol. 22, No. 11, 850-852, Jun. 1, 2010.

(D'Alessandro et al., 2015), "Polarization Independent Nematic Liquid Crystal Waveguides for Optofluidic Applications," IEEE Photonics, 2015, 27, 1-1.

(Di et al., 2018), "Review of Optical Fiber Sensors for Deformation Measurement," Optik: International Journal for Light and Electron Optics, 2018, 168, 703-713.

(Geng et al., 2012), "Two-Dimensional Bending Vector Sensing Based on Spatial Cascaded Orthogonal Long Period Fiber," Optics Express, Dec. 17, 2012 20(27), 28557-62.

(Gong et al., 2013), "An Optical Fiber Curvature Sensor Based on Photonic Crystal Fiber Modal Interferometer,"Sensors and Actuators A: Physical, 2013, 195, 139-141.

(Guo et al., 2017), "Highly Flexible and Stretchable Optical Strain Sensing for Human Motion Detection," Optica, 2017, vol. 4, Issue 10, 1285-1288.

(Guo et al., 2018), "Multiplexed Static FBG Strain Sensors by Dual-Comb Spectroscopy with a Free Running Fiber Laser," Optics Express, Jun. 25, 2018 26(13), 16147-16154.

(Missinne, 2014), "Stretchable Optical Waveguides," Optics Express, 2014, vol. 22, Issue 4, 4168-4179.

(Niu, 2014), "Curvature Sensor Based on Two Cascading Abrupt-Tapers Modal Interferometer in Single Mode Fiber," Optics Communications, 2014, vol. 333, Dec. 15, 2014, 11-15.

(Ou, 2013), "Ambient Refractive Index-Independent Bending Vector Sensor Based on Seven-Core Photonic Crystal Fiber Using Lateral Offset Splicing," Optics Express, Oct. 7, 2013, 2.

* cited by examiner

MOTION RECOGNITION CLOTHING WITH FLEXIBLE OPTICAL SENSORS

CROSS-REFERENCE TO RELATED APPLICATIONS

This patent application: (a) claims the priority benefit of provisional application 62/797,266 filed on 2019 Jan. 26; (b) claims the priority benefit of provisional application 62/727,798 filed on 2018 Sep. 6; and (c) is a continuation in part of application Ser. No. 16/010,448 filed on 2018 Jun. 16.

Application Ser. No. 16/010,448 claimed the priority benefit of provisional application 62/683,237 filed on 2018 Jun. 11. Application Ser. No. 16/010,448 claimed the priority benefit of provisional application 62/538,793 filed on 2017 Jul. 30. Application Ser. No. 16/010,448 was a continuation in part of application Ser. No. 15/702,081 filed on 2017 Sep. 12. Application Ser. No. 16/010,448 was a continuation in part of application Ser. No. 15/227,254 filed on 2016 Aug. 3 which is now U.S. Pat. No. 10,321,873 issued on 2019 Jun. 18. Application Ser. No. 15/702,081 was a continuation in part of application Ser. No. 14/795,373 filed on 2015 Jul. 9. Application Ser. No. 15/702,081 claimed the priority benefit of provisional application 62/538,793 filed on 2017 Jul. 30. Application Ser. No. 15/702,081 claimed the priority benefit of provisional application 62/449,735 filed on 2017 Jan. 24. Application Ser. No. 15/702,081 was a continuation in part of application Ser. No. 15/227,254 filed on 2016 Aug. 3 which is now U.S. Pat. No. 10,321,873 issued on 2019 Jun. 18. Application Ser. No. 15/227,254 claimed the priority benefit of provisional application 62/357,957 filed on 2016 Jul. 2. Application Ser. No. 15/227,254 was a continuation in part of application Ser. No. 14/73,6652 filed on 2015 Jun. 11. Application Ser. No. 15/227,254 was a continuation in part of application Ser. No. 14/664,832 filed on 2015 Mar. 21 which is now U.S. Pat. No. 9,582,072 issued on 2017 Feb. 28. Application Ser. No. 15/227,254 was a continuation in part of application Ser. No. 15/130,995 filed on 2016 Apr. 17 which is now U.S. Pat. No. 9,891,718 issued on 2018 Feb. 13. Application Ser. No. 15/227,254 was a continuation in part of application Ser. No. 15/079,447 filed on 2016 Mar. 24 which is now U.S. Pat. No. 10,234,934 issued on 2019 Mar. 19. Application Ser. No. 15/130,995 claimed the priority benefit of provisional application 62/150,886 filed on 2015 Apr. 22. Application Ser. No. 15/079,447 claimed the priority benefit of provisional application 62/150,886 filed on 2015 Apr. 22. Application Ser. No. 15/079,447 was a continuation in part of application Ser. No. 14/664,832 filed on 2015 Mar. 21 which is now U.S. Pat. No. 9,582,072 issued on 2017 Feb. 28. Application Ser. No. 15/079,447 was a continuation in part of application Ser. No. 14/463,741 filed on 2014 Aug. 20 which is now U.S. Pat. No. 9,588,582 issued on 2017 Mar. 7. Application Ser. No. 14/795,373 claimed the priority benefit of provisional application 62/187,906 filed on 2015 Jul. 2. Application Ser. No. 14/795,373 claimed the priority benefit of provisional application 62/182,473 filed on 2015 Jun. 20. Application Ser. No. 14/795,373 claimed the priority benefit of provisional application 62/086,053 filed on 2014 Dec. 1. Application Ser. No. 14/795,373 claimed the priority benefit of provisional application 62/065,032 filed on 2014 Oct. 17. Application Ser. No. 14/795,373 was a continuation in part of application Ser. No. 14/736,652 filed on 2015 Jun. 11. Application Ser. No. 14/736,652 claimed the priority benefit of provisional application 62/100,217 filed on 2015 Jan. 6. Application Ser. No. 14/736,652 claimed the priority benefit of provisional application 62/014,747 filed on 2014 Jun. 20. Application Ser. No. 14/736,652 was a continuation in part of application Ser. No. 14/664,832 filed on 2015 Mar. 21 which is now U.S. Pat. No. 9,582,072 issued on 2017 Feb. 28. Application Ser. No. 14/664,832 claimed the priority benefit of provisional application 61/976,650 filed on 2014 Apr. 8. Application Ser. No. 14/664,832 was a continuation in part of application Ser. No. 14/463,741 filed on 2014 Aug. 20 which is now U.S. Pat. No. 9,588,582 issued on 2017 Mar. 7. Application Ser. No. 14/463,741 claimed the priority benefit of provisional application 61/878,893 filed on 2013 Sep. 17. The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices and methods for human motion capture.

INTRODUCTION

There are many potential applications for devices which measure human motion, posture, and gestures. These potential applications include: athletic training and motion capture for sports which involve extensive lower-body motion (such as bicycling and soccer), extensive arm motion (such as tennis and golf), extensive lower-body motion (such as bicycling and running), extensive spinal motion, extensive forearm motion (such as tennis and golf), wrist motion (such as tennis, golf, and Frisbee), ankle motion (such as running and soccer), finger and hand motion (such as tennis, golf, baseball, and fencing), athletic performance measurement and improvement; and entertainment, gaming, and artistic applications (such as animated pictures, avatar animation, computer animation, computer gaming, dance instruction, dance performance, gaming input devices, graphical animation, motion capture, motion picture animation, motion pictures, movie making, performance arts, training and motion capture for playing musical instruments, virtual gaming, virtual reality); and health, fitness, and medical applications (such as avoidance of repeated motion injuries, biofeedback, biomechanical analysis, caloric expenditure measurement, caloric intake monitoring, cardiac function monitoring, congestive heart failure assessment, energy balance, ergonomic evaluation, fall prevention and detection, gait analysis, medical diagnosis, medical therapy, nutritional monitoring and improvement, orthopedic therapy, orthotic design and fitting, physical therapy, plethysmography, postoperative therapy, posture correction, pronation analysis, pulse monitoring, range of motion assessment, rehabilitation assessment, repetitive stress injury avoidance, respiratory function analysis, spinal injury avoidance, spinal motion assessment, telemedicine, telesurgery, virtual exercise, weight management); and human-computer interface and telecommunication (such as gesture recognition, telerobotics, telesurgery, telepresence, notifications, telecommunication, teleconferencing, telepresence, telerobotics, virtual commerce, and virtual reality interaction).

A first way to measure human motion, posture, and gestures is camera-based motion capture. Camera-based motion capture can be very accurate, but has limitations. For example, generally a person is constrained to stay within a given location which is within the field of view of the camera or cameras. Camera-based motion capture generally does not work well for a person who is running or going about the activities of daily life. Also, camera-based motion capture does not work well if portions of a person's body are obscured by other portions of the person's body or by matter in the environment. For example, camera-based motion capture does not work well for a person swimming.

A second way to measure human motion, posture, and gestures is inertial-based motion capture. Inertial-based motion capture requires that a person wear one or more inertial measurement units (IMUs) at one or more locations on their body. The more complex the motion, posture, or gesture that one wishes to measure, the more IMUs are required. IMUs often comprise an accelerometer and a gyroscope. There has been a lot of progress in inertial-based motion capture during the past several years, but several limitations still remain. For example, there can be a lag and/or drift between when a person moves and when this motion is captured by IMUs. Also, because an IMU measures motion at a single point (relative to one or more other points), measurement of complex motions, postures, and gestures can require a prohibitively-large number of IMUs.

A third way to measure human motion, posture, and gestures is based on strain, stretch, and/or bend sensors. In recent years, there has been work toward incorporating strain, stretch, and/or bend sensors into gloves and other clothing to measure human motion, posture, and gestures. This can enable measurement of human motion, posture, and gestures without the movement restrictions of camera-based motion capture and without the point-estimate constraints of IMUs. The vast majority of the prior art discloses strain, stretch, and/or bend sensors which measure human motion by measuring changes in the transmission of electrical energy through a conductive sensor. However, there can be lags, variability and hysteresis in the transmission of electrical energy through a stretchable and/or bendable sensor. There remains a need for strain, stretch, and/or bend sensors with less lag, variability, and hysteresis for more rapid and accurate measurement of human motion, posture, and gestures.

Review of the Prior Art

The general concept of optical strain, stretch, and/or bend sensors is not new. Although the vast majority of strain, stretch, and/or bend sensors in the prior art are based on transmission of electricity through sensors, there are examples of innovative prior art in the patent literature which disclose the general concept of using light transmission to measure stretching and bending. For example, U.S. Pat. No. 7,664,347 (Childers et al., Feb. 16, 2010; "Multi-Core Optical Fiber Sensor") discloses a multi-core optical fiber sensor with includes an optical fiber having at least two cores, wherein the cores have collocated measurement portions such as in-fiber interferometers or Bragg grating portions. U.S. Pat. No. 9,562,826 (Handerek, Feb. 7, 2017; "Distributed Optical Fibre Sensor") discloses optical fibre sensors with light pulses of different lengths. U.S. Pat. No. 9,743,860 (Keesling, Aug. 29, 2017; "Use of Light Transmission through Tissue to Sense Joint Flexure") discloses using light transmission thought tissue to detect the joint movement. U.S. Pat. No. 9,759,633 (Handerek, Sep. 12, 2017; "Distributed Optical Fibre Sensor") discloses optical fibre sensors with light pulses of different lengths. U.S. Patent Application No. 20150359455 (Hahami et al., Dec. 17, 2015; "Fiber Optic Shape Sensing Applications") discloses using fiber optic cables for motion tracking. U.S. Patent Application No. 20170350733 (Salomonsson, Dec. 7, 2017; "Sensor and Method Enabling the Determination of the Position and Orientation of a Flexible Element") discloses a bend sensor with at least two spatially separated light permeable tubes.

There is also innovative discussion of optical strain, stretch, and/or bend sensors in the non-patent literature. For example, Chen, 2010 ("Highly Sensitive Bend Sensor Based on Bragg Grating in Eccentric Core Polymer Fiber," IEEE Photonics Technology Letters, Vol. 22, No. 11, 850-852, Jun. 1, 2010) discloses an optical bend sensor with a Bragg grating inside an eccentric core polymer optical fiber. Also, d'Alessandro et al., 2015 ("Polarization Independent Nematic Liquid Crystal Waveguides for Optofluidic Applications," IEEE Photonics, 2015, 27, 1-1) discloses waveguides made from nematic liquid crystal in PDMS (polydimethylsiloxane) channels. Di et al., 2018 ("Review of Optical Fiber Sensors for Deformation Measurement," Optik: International Journal for Light and Electron Optics, 2018, 168, 703-713) review the developments of optical fiber sensors for curvature measurement during the past years, including advantages and limitations of different types of optical fiber sensors.

Also, Geng et al., 2012 ("Two-Dimensional Bending Vector Sensing Based on Spatial Cascaded Orthogonal Long Period Fiber," Optics Express, 2012 Dec. 17, 20 (27), 28557-62) discloses two-dimensional and three-dimensional bending vector sensors based on spatial cascaded orthogonal long period fiber gratings (SCO-LPFGs). Gong et al., 2013 ("An Optical Fiber Curvature Sensor Based on Photonic Crystal Fiber Modal Interferometer ("Sensors and Actuators A: Physical, 2013, 195, 139-141) disclose an optical fiber curvature sensor using a Photonic Crystal Fiber (PCF) modal interferometer. Guo et al., 2017 ("Highly Flexible and Stretchable Optical Strain Sensing for Human Motion Detection," Optica, 2017, Vol. 4, Issue 10, 1285-1288) disclose strain sensors using dye-doped PDMS (polydimethylsiloxane) optical fiber. Guo et al., 2018 ("Multiplexed Static FBG Strain Sensors by Dual-Comb Spectroscopy with a Free Running Fiber Laser," Optics Express, 2018 Jun. 25, 26 (13), 16147-16154) disclose multiplexed static strain sensing using dual-comb spectroscopy.

Also, Missinne, 2014 ("Stretchable Optical Waveguides," Optics Express, 2014, Vol. 22, Issue 4, 4168-4179. disclose mechanically stretchable optical waveguides using PDMS (polydimethylsiloxane). Niu, 2014 ("Curvature Sensor Based on Two Cascading Abrupt-Tapers Modal Interferometer in Single Mode Fiber," Optics Communications, 2014, Vol. 333, Dec. 15, 2014, 11-15) disclose a curvature sensor based on two cascading abrupt-tapers modal interferometers in a single mode fiber (SMF). Ou, 2013 ("Ambient Refractive Index-Independent Bending Vector Sensor Based on Seven-Core Photonic Crystal Fiber Using Lateral Offset Splicing," Optics Express, Oct. 7, 2013, 21 (20), 23812-21) disclose an optical fiber directional bending vector sensor based on a Mach-Zehnder interferometer (MZI). Wang et al, 2018 ("Review of Optical Fiber Bending/Curvature Sensor," Measurement, 2018, 130) review optical fiber bending sensors, including the advantages and disadvantages of various sensors. Wang et al., 2018 ("Self-Organized Structures of Soliton Molecules in 2-m Fiber Laser Based on Mos2 Saturable Absorber," IEEE Photonics Technology Letters, Jul. 1, 2018, Vol. 30, No. 13, 1210-1213) disclose self-organized structures of soliton molecules in a thulium-doped fiber laser mode.

Further, Xu et al., 2017 ("Dual-Layer Orthogonal Fiber Bragg Grating Mesh Based Soft Sensor for 3-Dimensional Shape Sensing," Optics Express, 2017, Vol. 25, Issue 20, 24727-24734) disclose a soft shape sensor for 3-dimensional object shape measurement. Yoon, 2018 ("Elastomer Thin-Film Pressure Sensor Based on Embedded Photonic Tunnel-Junction Arrays," Optics Letters, 2018, Vol. 43, Issue 16, 3953-3956) disclose an elastomer thin-film pressure sensor enabled by pressure-sensitive optical signals through vertical photonic tunnel junction couplers. Zhao, 2017 ("Fabrication, Sensation and Control of Fluidic Elastomer Actuators and Their Application towards Hand Orthotics and Prosthetics," Cornell Dissertation, 2017, Ph.D., Mechanical Engineering) discloses a cuboid soft actuator and a soft orthotic finger with position control enabled via an embedded optical fiber.

SUMMARY OF THE INVENTION

Although the prior art discusses general concepts and designs for optical sensors, designing optical strain, stretch and/or bend sensors for incorporation into clothing to measure human motion, posture, and gestures involves some specific challenges. For example, wearable strain, stretch, and/or bend sensors must be flexible and/or stretchable so that they do not impede human movement. They also must be sufficiently compact to be woven or otherwise incorporated into smart clothing. They must also be sufficiently long to span human body joints. There are also issues with respect to multi-sensor configurations to measure rotational joint movement. This invention addresses these design challenges by disclosing innovative designs for flexible optical sensors which can be incorporated into motion recognition clothing. Wearable optical strain, stretch, and/or bend sensors can potentially provide more precise and consistent measurement of human motion, posture, and gestures without the locational limitations of camera-based motion capture, the point-estimate limitations of inertial-based methods, and the variability of electrically-conductive strain, stretch, and/or bend sensors.

This invention can be embodied in a wearable flexible optical sensor for measuring human motion comprising: a bendable longitudinal light channel through which light energy is transmitted; wherein the bendable longitudinal light channel is configured to be worn across a human body joint; wherein the bendable longitudinal light channel is configured to span the human body joint in a longitudinal manner; wherein changes in light energy transmitted through the bendable longitudinal light channel are used to measure motion of the human body joint; and wherein there is longitudinal variation in the material, shape, and/or structure of the bendable longitudinal light channel along the longitudinal axis of the bendable longitudinal optical sensor. In an example, there can be cross-sectional variation in the material, shape, and/or structure of the bendable longitudinal light channel around the cross-sectional circumference of the bendable longitudinal optical sensor. In an example, the bendable longitudinal light channel can be made from polydimethylsiloxane (PDMS) which is impregnated and/or doped with light-absorbing, light-reflecting, or light-polarizing material.

DETAILED DESCRIPTION

In an example, a wearable flexible optical sensor for measuring human motion can span (the surface of a body member which contains) a body joint. In an example, a wearable flexible optical sensor for measuring human motion can span (the surface of a body member which contains) a body joint in a longitudinal manner. In an example, a wearable flexible optical sensor spanning a body joint in a longitudinal manner. In an example, a wearable flexible optical sensor spanning a body joint in a longitudinal manner can mean that the sensor has a longitudinal axis which is substantially parallel to the central longitudinal axis of the body joint when the body joint is maximally extended, such as in the posture of the Vitruvian Man by Leonardo da Vinci. In an example, a wearable flexible optical sensor for measuring human motion can span a body joint in an oblique manner. In an example, a wearable flexible optical sensor spanning a body joint in an oblique manner can mean that the sensor has a longitudinal axis which intersects (a virtual line parallel to) the central longitudinal axis of the body joint at an oblique angle.

In an example, a wearable device for measuring human motion can comprise a plurality of wearable flexible optical sensors which all span the same body joint, but span the joint at different locations around the circumference of the (body member containing the) joint. In an example, a wearable device for measuring human motion can comprise four wearable flexible optical sensors: a first sensor which spans the ventral surface of the joint, a second sensor which spans the dorsal surface of the joint, and third and forth sensors which span opposing-side lateral surfaces of the joint. In an example, a wearable device for measuring human motion can comprise four wearable flexible optical sensors: a first sensor which spans the ventral surface of the joint in a longitudinal manner, a second sensor which spans the dorsal surface of the joint in a longitudinal manner, and third and forth sensors which span opposing-side lateral surfaces of the joint in a longitudinal manner. In an example, a wearable device for measuring human motion can further comprise one or more wearable flexible optical sensors which span the body joint in an oblique manner. In an example, a wearable device for measuring human motion can further comprise one or more wearable flexible optical sensors which span the body joint in a helical manner.

In an example, a wearable flexible optical sensor for measuring human motion can be a flexible optical fiber. In an example, a wearable flexible optical sensor for measuring human motion can be made from a transparent polymer. In an example, a wearable flexible optical sensor can be made from urethane rubber. In an example, a wearable flexible optical sensor can be made from silicone and/or polydimethylsiloxane (PDMS). In an example, a wearable flexible optical sensor can be made from a first (substantially transparent) material which is mixed, doped, or impregnated with a second (light-absorbing, light-reflecting, or light-polarizing) material. In an example, light-absorbing material can be a dye or contrast media. In an example, a wearable flexible optical sensor can be made from polydimethylsiloxane (PDMS) which is mixed or doped with dye. In an example, a light-reflecting material can be micro-crystals. In an example, a wearable flexible optical sensor can be made from polydimethylsiloxane (PDMS) which is mixed or impregnated with micro-crystals or micro-lenses. In an example, micro-crystals or micro-lenses within a transparent polymer can be given a selected orientation by exposing them to an electromagnetic field before or during curing in order to achieve desired reflective or refractive effects.

In an example, a wearable flexible optical sensor for measuring human motion can be made from one or more materials selected from the group consisting of: dye, nematic liquid crystal, photonic crystal, platinum-catalyzed silicone, polybutylene adipate terephthalate, polybutylene adipate-co-terephthalate, polybutyrate, polydimethylsiloxane (PDMS), silicone, and thermoplastic. In an example, the core and/or cladding of a wearable flexible optical sensor for measuring human motion can be made from one or more materials selected from the group consisting of: dye, nematic liquid crystal, photonic crystal, platinum-catalyzed silicone, polybutylene adipate terephthalate, polybutylene adipate-co-terephthalate, polybutyrate, polydimethylsiloxane (PDMS), silicone, and thermoplastic.

In an example, a wearable flexible optical sensor for measuring human motion can be elastic and/or stretchable. In an example, a wearable flexible optical sensor for measuring human motion can have a first configuration with a first length and a second configuration with a second length, wherein light energy transmitted through the sensor has a first power level, intensity level, phase, wavelength, and/or spectrum in the first configuration and a second power level, intensity level, phase, wavelength, and/or spectrum in the second configuration.

In an example, a wearable flexible optical sensor for measuring human motion can have a first configuration with a first bend radius and a second configuration with a second bend radius, wherein light energy transmitted through the sensor has a first power level, intensity level, phase, wavelength, and/or spectrum in the first configuration and a second power level, intensity level, phase, wavelength, and/or spectrum in the second configuration. In an example, a wearable flexible optical sensor for measuring human motion can have a first configuration with a first amount of concavity (or convexity) and a second configuration with a second amount of concavity (or convexity), wherein light energy transmitted through the sensor has a first power level, intensity level, phase, wavelength, and/or spectrum in the first configuration and a second power level, intensity level, phase, wavelength, and/or spectrum in the second configuration.

In an example, a wearable flexible optical sensor for measuring human motion can measure bending and/or rotation of a body joint which the sensor spans. In an example, bending and/or rotation of a body joint can elongate, bend, twist, or otherwise deform a wearable flexible optical sensor which spans this body joint. In an example, elongation, bending, twisting, or other deformation of the wearable flexible optical sensor causes changes in the power, intensity, phase, wavelength, and/or spectrum of light energy transmitted through wearable flexible optical sensor. In an example, these changes in light energy power, intensity, phase, wavelength, and/or spectrum can be analyzed to measure bending and/or rotation of the body joint.

In an example, elongation, bending, and/or twisting of a wearable flexible optical sensor can be measured by changes in one or more metrics selected from the group consisting of: loss of intensity or power of light transmitted through the channel; change in the wavelength of light transmitted through the channel; change in the spectrum of light transmitted through the channel; and change in the polarity, coherence, or orientation of light transmitted through the channel. In an example, changes in one or more of the above metrics in respect to elongation, bending, and/or twisting of the light channel can be non-linear. In an example, the power or intensity of light transmitted through a light channel can decrease as the light channel is elongated and/or stretched. In an example, the power or intensity of light transmitted through a light channel can decrease when a light channel is bent in a first direction and can increase when the light channel is bent in a second direction. In an example, the power or intensity of light transmitted through a light channel can decrease when a light channel is bent in a concave manner and can increase when the light channel is bent in a convex manner, or vice versa.

In an example, there may be little change in the above metrics with small levels of elongation, bending, and/or twisting. In an example, there can be a critical bending radius before which the above metrics do not substantively change, but after which the above metrics do change. In an example, a first metric can be more accurate for measuring smaller amounts of elongation, bending, and/or twisting and a second metric can be more accurate for measuring larger amounts of elongation, bending, and/or twisting. In an example, changes in the spectrum of light energy transmitted through a light channel can be used to measure smaller amounts of elongation, bending, and/or twisting, while changes in the power or intensity of light transmitted through the light channel can be used to measure larger amounts of elongation, bending, and/or twisting. In an example, combined measurement and multivariate analysis of two of the above metrics can provide more accurate measuring of elongation, bending, and/or twisting over a wider range of motion than is possible with a single metric.

In an example, a wearable flexible optical sensor can further comprise a light emitter which emits light into a first end (or first longitudinal portion) of a wearable flexible optical sensor and a light receiver which receives light from a second end (or second longitudinal portion) of the wearable flexible optical sensor. In an example, a light emitter can be selected from the group consisting of: light emitting diode, ($CO_2$ or ultraviolet) laser, active matrix organic light-emitting diode, amplified spontaneous emission light source, broadband light source, collimated light projector, organic light emitting diode, passive matrix light-emitting diode, transmission holographic optical element, and vertical-cavity surface-emitting laser. In an example, a light receiver can be selected from the group consisting of: germanium photodiode, indium gallium arsenide photodiode, mercury cadmium telluride photodiode, photodarlington photodetector, optical spectrum analyzer, silicon photodiode, and spectroscopic sensor.

In an example, a wearable flexible optical sensor through which light energy is transmitted can be a bendable longitudinal optical fiber. In an example, a wearable flexible optical sensor can have a proximal end (proximal relative to a body joint which it spans) and a distal end (distal relative to the body joint). In an example, such a sensor can further comprise a light emitter which emits light energy into the proximal end and a light receiver which receives light energy from the distal end, or vice versa. In an example, a wearable flexible optical sensor can have two ends which are both proximal relative to the body joint which it spans. In an example, there can be a loop between these two proximal ends, wherein this loop spans the body joint. In an example, a light emitter can emit light energy into a first proximal end of a sensor and a light receiver can receive light energy from a second proximal end of the sensor. In an example, a wearable flexible optical sensor can have two ends which are both distal relative to the body joint which it spans, with a loop between them which spans the body joint. In an example, a light emitter can emit light energy into a first distal end and a light receiver can receive light energy from the second distal end.

In an example, there can be longitudinal variation in the material of a wearable flexible optical sensor along the longitudinal axis of the wearable flexible optical sensor. In an example, there can be periodic and/or repeated longitudinal variation in the material of a wearable flexible optical sensor along the longitudinal axis of the wearable flexible optical sensor. In an example, there can be variation in reflectivity along the longitudinal axis of the wearable flexible optical sensor. In an example, there can be periodic and/or repeated variation in reflectivity along the longitudinal axis of the wearable flexible optical sensor.

In an example, a wearable flexible optical sensor can include a Bragg grating. In an example, elongation, bending, and/or twisting of a wearable flexible optical sensor can be measured by shifts in the spectrum of light passing through a Bragg grating in the wearable flexible optical sensor. In an example, there can be a single Bragg grating in a wearable flexible optical sensor. In an example, there can be multiple Bragg gratings in a wearable flexible optical sensor, wherein these Bragg gratings differ in periodicity and/or orientation. In an example, a wearable flexible optical sensor with multiple Bragg gratings with different orientations can differentiate between elongation, bending, and/or twisting of the wearable flexible optical sensor in different directions.

In an example, there can be periodic longitudinal variation in the refractive index of a wearable flexible optical sensor. In an example, there can be periodic lateral (or cross-sectional or radial) variation in the refractive index of a wearable flexible optical sensor. In an example, longitudinal variation in refractive index can comprise a first Bragg grating in a wearable flexible optical sensor and lateral (or cross-sectional or radial) variation in refractive index can comprise a second Bragg grating in the wearable flexible optical sensor. In an example, the combination of longitudinal and lateral (or cross-sectional or radial) Bragg gratings can enable measurement of three-dimensional shape and movement.

In an example, a wearable flexible optical sensor can comprise a three-dimensional array of micro-mirrors to achieve desired reflective effects for measurement of three-dimensional movement. In an example, a wearable flexible optical sensor can comprise a three-dimensional array of micro-mirrors with different orientations to achieve desired reflective effects for measurement of three-dimensional movement. In an example, a wearable flexible optical sensor can comprise a three-dimensional array of micro-lenses to achieve desired refractive effects for measurement of three-dimensional movement. In an example, a wearable flexible optical sensor can comprise a three-dimensional array of micro-lenses with different orientations to achieve desired refractive effects for measurement of three-dimensional movement.

In an example, a wearable flexible optical sensor can comprise an interferometer. In an example, light energy passing through a wearable flexible optical sensor can be split and then recombined. In an example, spectral and/or intensity differences between light before splitting and after recombination can be compared to measure elongation, bending, and/or twisting of the light channel. In an example, a wearable flexible optical sensor can comprise an optical structure selected from the group consisting of: Fabry-Perot interferometer, long period fiber grating, Mach-Zehnder interferometer, Michelson interferometer, and Sagnac interferometer.

In an example, there can be longitudinal variation in the cross-sectional size of a wearable flexible optical sensor along the longitudinal axis of the wearable flexible optical sensor. In an example, a wearable flexible optical sensor can have one or more tapered segments. In an example, a wearable flexible optical sensor can have two longitudinally-symmetric tapered segments. In an example, a first segment of a wearable flexible optical sensor can have a first cross-segmental area and a second segment can have a second cross-segmental area, wherein the second area is larger than the first area.

In an example, there can be longitudinal variation in the cross-segmental shape of a wearable flexible optical sensor along the longitudinal axis of the wearable flexible optical sensor. In an example, a first segment of a wearable flexible optical sensor can have a convex cross-segmental shape and a second segment can have a concave cross-segmental shape. In an example, a first segment of a wearable flexible optical sensor can have a first cross-segmental curvature and a second segment can have a second cross-segmental curvature, wherein the second segment has a smaller curvature radius than the first segment. In an example, the can be multiple longitudinal segments of a wearable flexible optical sensor. In an example, these segments can be connected in a radially asymmetric manner. In an example, connections between these segments can be axially-offset relative to each other. In an example, a connection between adjacent segments can be radially-asymmetric or axially-offset.

In an example, the cladding of a wearable flexible optical sensor can be asymmetric and/or eccentric. In an example, the material, thickness, refraction, smoothness/roughness, and/or shape of cladding can be asymmetric with respect to a central longitudinal axis of a wearable flexible optical sensor. In an example, a first portion of the cladding on a wearable flexible optical sensor which is configured to be worn a first distance from the surface of a person's body can be made from a first material and a second portion of this cladding which is configured to be worn a second distance from the surface of the person's body can be made from a second material, wherein the second material is different than the first material.

In an example, a first portion of the cladding on a wearable flexible optical sensor which is configured to be worn a first distance from the surface of a person's body can have first refraction index and a second portion of this cladding which is configured to be worn a second distance from the surface of the person's body can have a second refraction index, wherein the second refraction index is at least 10% greater than the first refraction index. In an example, there can be cross-sectional variation in the reflectivity of a wearable flexible optical sensor around the cross-sectional circumference of the wearable flexible optical sensor. In an example, a first portion of the cross-sectional perimeter of a wearable flexible optical sensor can have a first level of reflectivity and a second portion of the cross-sectional perimeter of a wearable flexible optical sensor can have a second level of reflectivity, wherein the second level is greater than the first level. In an example, a first portion of the cross-sectional perimeter of a wearable flexible optical sensor can be clad with a material with a first refractive index and a second portion of the cross-sectional perimeter of a wearable flexible optical sensor can be clad with a material with a second refractive index, wherein the second refractive index is greater than the first level. In an example, the first portion can be configured to be worn closer to the surface of a person's body and the second portion can be configured to be worn father from the person's body, or vice versa.

In an example, a first portion of the cross-sectional perimeter of a wearable flexible optical sensor can be clad with a material with a first refractive index and a second portion of the cross-sectional perimeter of a wearable flexible optical sensor can be clad with a material with a second refractive index, wherein the second refractive index is greater than the first level. In an example, a first portion of the cross-sectional perimeter of a wearable flexible optical sensor can have a first waveguide numerical aperture and a second portion of the cross-sectional perimeter of a wearable flexible optical sensor which is configured to be worn farthest from the surface of a person's body can have a second waveguide numerical aperture. In an example, the first portion can be configured to be worn closer to the surface of a person's body and the second portion can be configured to be worn father from the person's body, or vice versa. In an example, a wearable flexible optical sensor can be anisotropic.

In an example, a first portion of the cladding on a wearable flexible optical sensor which is configured to be worn a first distance from the surface of a person's body can have a first level of smoothness and a second portion of this cladding which is configured to be worn a second distance from the surface of the person's body can have a second level of smoothness index, wherein the second level is greater than the first level. In an example, a first portion of the cladding on a wearable flexible optical sensor which is configured to be worn a first distance from the surface of a person's body which is cut, roughened, or abraded to a first degree and a second portion of this cladding which is configured to be worn a second distance from the surface of the person's body which cut, roughened, or abraded to a second degree, wherein the second degree is less than the first degree.

In an example, a first portion of the cladding on a wearable flexible optical sensor which is configured to be worn a first distance from the surface of a person's body with a first degree of concavity (or convexity) and a second portion of this cladding which is configured to be worn a second distance from the surface of the person's body with a second degree of concavity (or convexity), wherein the second degree is less than the first degree. In an example, a first portion of the cladding on a wearable flexible optical sensor which is configured to be worn a first distance from the surface of a person's body with a first frequency (or density or periodicity) of undulations and a second portion of this cladding which is configured to be worn a second distance from the surface of the person's body with a first frequency (or density or periodicity) of undulations, wherein the second degree is less than the first degree.

In an example, the core of a wearable flexible optical sensor can be asymmetric and/or eccentric. In an example, the material and/or shape of core can be asymmetric with respect to a central longitudinal axis of a wearable flexible optical sensor. In an example, a first portion of the core on a wearable flexible optical sensor which is configured to be worn a first distance from the surface of a person's body can be made from a first material and a second portion of this core which is configured to be worn a second distance from the surface of the person's body can be made from a second material, wherein the second material is different than the first material.

In an example, a first portion of the core on a wearable flexible optical sensor which is configured to be worn a first distance from the surface of a person's body can have first refraction index and a second portion of this core which is configured to be worn a second distance from the surface of the person's body can have a second refraction index, wherein the second refraction index is at least 10% greater than the first refraction index. In an example, a first portion of the core on a wearable flexible optical sensor which is configured to be worn a first distance from the surface of a person's body can have a first level of smoothness and a second portion of this core which is configured to be worn a second distance from the surface of the person's body can have a second level of smoothness index, wherein the second level is greater than the first level.

In an example, a first portion of the core on a wearable flexible optical sensor which is configured to be worn a first distance from the surface of a person's body which is cut, roughened, or abraded to a first degree and a second portion of this core which is configured to be worn a second distance from the surface of the person's body which cut, roughened, or abraded to a second degree, wherein the second degree is less than the first degree. In an example, a first portion of the core on a wearable flexible optical sensor which is configured to be worn a first distance from the surface of a person's body with a first degree of concavity (or convexity) and a second portion of this core which is configured to be worn a second distance from the surface of the person's body with a second degree of concavity (or convexity), wherein the second degree is less than the first degree. In an example, a first portion of the core on a wearable flexible optical sensor which is configured to be worn a first distance from the surface of a person's body with a first frequency (or density or periodicity) of undulations and a second portion of this core which is configured to be worn a second distance from the surface of the person's body with a first frequency (or density or periodicity) of undulations, wherein the second degree is less than the first degree.

In an example, there can be an arcuate structure within a section of a core of a wearable flexible optical sensor, wherein this arcuate structure is made from a material which has a different refractive index than the material which comprises the rest of the core. In an example, the shape of this arcuate structure can be selected from the group consisting of: sphere; ellipsoid; ovaloid; paraboloid; and cylinder. In an example, this arcuate structure can be made from a material with a lower refractive index than the rest of the core. In an example, this arcuate structure can be hollow. In an example, this arcuate structure can be a hole in the core.

In an example, a first portion of the cross-sectional perimeter of a wearable flexible optical sensor can have a first shape and a second portion of the cross-sectional perimeter of a wearable flexible optical sensor can have a second shape. In an example, the second shape can be more arcuate than the first shape. In an example, the second shape can be smoother (e.g. less rough) than the first shape. In an example, a first portion can be diametrically opposite from a second portion across the cross-sectional center of a wearable flexible optical sensor. In an example, the first portion can be configured to be worn closer to the surface of a person's body and the second portion can be configured to be worn father from the person's body, or vice versa.

In an example, there can be cross-sectional variation in the shape of a wearable flexible optical sensor around the cross-sectional circumference of the wearable flexible optical sensor. In an example, a wearable flexible optical sensor can have cross-sectional and/or core eccentricity. In an example, a wearable flexible optical sensor can have one or more portions whose cross-sections are asymmetric with respect to the central longitudinal axis of the channel. In an example, a wearable flexible optical sensor can be used to detect the direction of bending of a body joint by being asymmetric with respect to its central longitudinal axis. In an example, bending of a wearable flexible optical sensor in different directions (e.g. concave vs. convex) causes different changes in light energy transmission due to the cross-sectional asymmetry of the wearable flexible optical sensor.

In an example, connections or splices between segments of a wearable flexible optical sensor can be offset and/or asymmetric. In an example, a connection or splice between a single-core segment of a wearable flexible optical sensor and a multi-core segment of the wearable flexible optical sensor can be offset and/or asymmetric. In an example, a connection or splice between a single-core segment of a wearable flexible optical sensor and a multi-core segment of the wearable flexible optical sensor can be offset and/or asymmetric with respect to a central longitudinal axis of the wearable flexible optical sensor. In an example, a central longitudinal axis of a single-core segment of a wearable flexible optical sensor can be configured to be worn a first distance from the surface of a person's body and a central longitudinal axis of an adjacent a multi-core segment of the wearable flexible optical sensor can be configured to be worn a second distance from the surface of the person's body, wherein the second distance is greater than the first distance (or vice versa).

In an example, a wearable flexible optical sensor for measuring motion of the human body can comprise multiple substantially-parallel light channels. In an example, a wearable flexible optical sensor for measuring motion of the human body can comprise a multi-core optical fiber. In an example, a wearable flexible optical sensor for measuring motion of the human body can comprise a plurality of substantially parallel light channels. In an example, a wearable flexible optical sensor for measuring human motion can comprise an optical fiber with two substantially parallel cores or light channels. In an example, a wearable flexible optical sensor for measuring human motion can comprise an optical fiber with three substantially parallel cores or light channels. In an example, a wearable flexible optical sensor for measuring human motion can comprise an optical fiber with six substantially parallel cores or light channels. In an example, a wearable flexible optical sensor for measuring human motion can comprise an optical fiber with a plurality of substantially parallel cores or light channels whose cross-sections are distributed in a radially symmetric manner around a central longitudinal axis of the sensor.

In an example, a wearable deformable sensor for measuring motion of the human body in three-dimensions can have multiple substantially-orthogonal light channels. In an example, a wearable flexible optical sensor for measuring motion of the human body can comprise an orthogonal mesh, grid, or weave of optical fibers or light channels. In an example, a wearable flexible optical sensor for measuring motion of the human body can comprise an orthogonal mesh, grid, or weave of optical fibers or light channels. In an example, a wearable deformable sensor for measuring motion of the human body in three-dimensions can comprise a hexagonal (e.g. honeycomb) mesh, grid, or weave of optical fibers or light channels. In an example, a wearable deformable sensor for measuring motion of the human body in three-dimensions can comprise a helical optical fiber or light channel.

In an example, a wearable flexible optical sensor for measuring motion of the human body can comprise a first segment with a single light channel (e.g. single core segment) and a second segment with a plurality of light channels (e.g. multi-core segment). In an example, first and second segments can be axially aligned where they connect to each other. In an example, first and second segments can be axially-offset where they connect to each other. In an example, a wearable flexible optical sensor for measuring motion of the human body can have a sequence of three segments comprising: a first segment with a single light channel (e.g. single core segment); a second segment with a plurality of light channels (e.g. multi-core segment); and a third segment with a single light channel (e.g. single core segment).

In an example, a wearable flexible optical sensor for measuring human motion can comprise: a bendable longitudinal light channel through which light energy is transmitted, wherein the bendable longitudinal light channel is configured to be worn across a human body joint, wherein the bendable longitudinal light channel is configured to span the human body joint in a longitudinal manner; and wherein changes in the amount of light energy transmitted through the bendable longitudinal light channel are used to measure motion of the human body joint.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the amount (e.g. power, intensity, and/or transmission loss) of light energy transmitted through the bendable longitudinal light channel are used to measure motion (e.g. bending or rotation) of the human body joint; and wherein there is longitudinal variation in the material and/or reflectivity of the bendable longitudinal light channel along the longitudinal axis of the bendable longitudinal optical sensor.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the amount (e.g. power, intensity, and/or transmission loss) of light energy transmitted through the bendable longitudinal light channel are used to measure motion (e.g. bending or rotation) of the human body joint; wherein the bendable longitudinal light channel is made from a silicone material; and wherein the silicone is impregnated (e.g. doped) with light-absorbing, light-reflecting, or light-polarizing material.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the amount (e.g. power, intensity, and/or transmission loss) of light energy transmitted through the bendable longitudinal light channel are used to measure motion (e.g. bending or rotation) of the human body joint; and wherein there is cross-sectional variation in the reflectivity and/or shape of the bendable longitudinal light channel around the cross-sectional circumference of the bendable longitudinal.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the amount (e.g. power, intensity, and/or transmission loss) of light energy transmitted through the bendable longitudinal light channel are used to measure motion (e.g. bending or rotation) of the human body joint; and wherein there is cross-sectional variation in the material of the bendable longitudinal light channel around the cross-sectional circumference of the bendable longitudinal optical sensor.

In an example, a wearable flexible optical sensor for measuring human motion can comprise: a bendable longitudinal light channel through which light energy is transmitted; wherein the bendable longitudinal light channel is configured to be worn across a human body joint; wherein the bendable longitudinal light channel is configured to span the human body joint in a longitudinal manner; wherein changes in the amount of light energy transmitted through the bendable longitudinal light channel are used to measure motion of the human body joint; and wherein there are radially asymmetric (e.g. axially-offset) connections between longitudinal segments of the bendable longitudinal light channel or between the bendable longitudinal light channel and adjacent longitudinal light-transmitting channels.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the amount (e.g. power, intensity, and/or transmission loss) of light energy transmitted through the bendable longitudinal light channel are used to measure motion (e.g. bending or rotation) of the human body joint; and wherein there is longitudinal variation in the cross-sectional size and/or shape of the bendable longitudinal light channel along the longitudinal axis of the bendable longitudinal optical sensor.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; and wherein there is longitudinal variation in the material and/or reflectivity of the bendable longitudinal light channel along the longitudinal axis of the bendable longitudinal optical sensor.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; and wherein there is longitudinal variation in the cross-sectional size and/or shape of the bendable longitudinal light channel along the longitudinal axis of the bendable longitudinal optical sensor.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; and wherein there are radially asymmetric (e.g. axially-offset) connections between longitudinal segments of the bendable longitudinal light channel or between the bendable longitudinal light channel and adjacent longitudinal light-transmitting channels.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; and wherein there is cross-sectional variation in the reflectivity and/or shape of the bendable longitudinal light channel around the cross-sectional circumference of the bendable longitudinal light channel (e.g. cross-sectional radial asymmetry and/or core eccentricity).

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; and wherein there is cross-sectional variation in the material of the bendable longitudinal light channel around the cross-sectional circumference of the bendable longitudinal optical sensor.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; wherein the bendable longitudinal light channel further comprises a Bragg grating; and wherein elongation, bending, and/or twisting of the bendable longitudinal light channel changes the spectrum of light energy transmitted through the Bragg grating in the bendable longitudinal channel.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; and wherein there is longitudinal variation in the cross-sectional size and/or shape of the bendable longitudinal light channel along the longitudinal axis of the bendable longitudinal optical sensor.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; and wherein there is longitudinal variation in the material and/or reflectivity of the bendable longitudinal light channel along the longitudinal axis of the bendable longitudinal optical sensor.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; and wherein there are radially asymmetric (e.g. axially-offset) connections between longitudinal segments of the bendable longitudinal light channel or between the bendable longitudinal light channel and adjacent longitudinal light-transmitting channels.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; and wherein there is cross-sectional variation in the reflectivity and/or shape of the bendable longitudinal light channel around the cross-sectional circumference of the bendable longitudinal light channel (e.g. cross-sectional radial asymmetry and/or core eccentricity).

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint;

and wherein there is cross-sectional variation in the material of the bendable longitudinal light channel around the cross-sectional circumference of the bendable longitudinal optical sensor.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and wherein changes in the spectrum of light energy caused by transmission of the light energy through the bendable longitudinal light channel are used to measure motion (e.g. bending or rotation) of the human body joint.

In an example, a wearable flexible optical sensor for measuring human motion can comprise: a bendable longitudinal light channel through which light energy is transmitted (e.g. a bendable longitudinal optical fiber); wherein the bendable longitudinal light channel is configured to be worn across a human body joint; wherein the bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); wherein changes in the spectrum of light energy caused by transmission of the light energy through the bendable longitudinal light channel are used to measure motion (e.g. bending or rotation) of the human body joint; wherein the bendable longitudinal light channel is made from silicone (e.g. polydimethylsiloxane or PDMS); and wherein the silicone is impregnated (e.g. doped) with light-absorbing, light-reflecting, or light-polarizing material (e.g. dye or crystals).

In an example, a wearable flexible optical sensor for measuring human motion can comprise: a bendable multi-core optical sensor with multiple light-energy channels through which light energy is transmitted; wherein the bendable multi-core optical sensor is configured to be worn across a human body joint; wherein the bendable multi-core optical sensor is configured to span the human body joint in a longitudinal manner; wherein changes in the amount (e.g. power, intensity, and/or transmission loss) of light energy transmitted through the bendable multi-core optical sensor are used to measure motion (e.g. bending or rotation) of the human body joint; and wherein there is longitudinal variation in the number of light-energy channels along a longitudinal axis of the bendable multi-core optical sensor.

In an example, a wearable flexible optical sensor for measuring human motion can comprise: a bendable multi-core optical sensor with multiple light-energy channels through which light energy is transmitted; wherein the bendable multi-core optical sensor is configured to be worn across a human body joint; wherein the bendable multi-core optical sensor is configured to span the human body joint in a longitudinal manner; wherein changes in the spectrum of light energy caused by transmission of the light energy through the bendable multi-core optical sensor are used to measure motion (e.g. bending or rotation) of the human body joint; and wherein there is longitudinal variation in the number of light-energy channels along a longitudinal axis of the bendable multi-core optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein the first and/or second bendable longitudinal light channels is made from silicone (e.g. polydimethylsiloxane or PDMS); and wherein the silicone is impregnated (e.g. doped) with light-absorbing, light-reflecting, or light-polarizing material (e.g. dye or crystals).

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; and wherein changes in the amount (e.g. power, intensity, and/or transmission loss) of light energy transmitted through the first and/or second bendable longitudinal light channels are used to measure motion (e.g. bending or rotation) of the human body joint; and wherein there is longitudinal variation in the number of light-energy channels along a longitudinal axis of a bendable longitudinal multi-core optical sensor with multiple light-energy channels (including the first and second bendable longitudinal light channels) which spans the human joint.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; and wherein changes in the spectrum of light energy caused by transmission of the light energy through the first and/or second bendable longitudinal light channels are used to measure motion (e.g. bending or rotation) of the human body joint; and wherein there is longitudinal variation in the number of light-energy channels along a longitudinal axis of a bendable longitudinal multi-core optical sensor with multiple light-energy channels (including the first and second bendable longitudinal light channels) which spans the human joint.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the amount (e.g. power, intensity, and/or transmission loss) of light energy transmitted through the first and/or second bendable longitudinal light channels are used to measure motion (e.g. bending or rotation) of the human body joint; and wherein there is longitudinal variation in the material and/or reflectivity of the first and/or second bendable longitudinal light channels along the longitudinal axis of the first and/or second bendable longitudinal optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the amount (e.g. power, intensity, and/or transmission loss) of light energy transmitted through the first and/or second bendable longitudinal light channels are used to measure motion (e.g. bending or rotation) of the human body joint; and wherein there is longitudinal variation in the cross-sectional size and/or shape of the first and/or second bendable longitudinal light channels along the longitudinal axis of the first and/or second bendable longitudinal optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the amount (e.g. power, intensity, and/or transmission loss) of light energy transmitted through the first and/or second bendable longitudinal light channels are used to measure motion (e.g. bending or rotation) of the human body joint; and wherein there are radially asymmetric (e.g. axially-offset) connections between longitudinal segments of the first and/or second bendable longitudinal light channels or between the first and/or second bendable longitudinal light channels and adjacent longitudinal light-transmitting channels.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the amount (e.g. power, intensity, and/or transmission loss) of light energy transmitted through the first and/or second bendable longitudinal light channels are used to measure motion (e.g. bending or rotation) of the human body joint; and wherein there is cross-sectional variation in the reflectivity and/or shape of the first and/or second bendable longitudinal light channels around the cross-sectional circumference of the first and/or second bendable longitudinal light channel (e.g. cross-sectional radial asymmetry and/or core eccentricity).

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the amount (e.g. power, intensity, and/or transmission loss) of light energy transmitted through the first and/or second bendable longitudinal light channels are used to measure motion (e.g. bending or rotation) of the human body joint; and wherein there is cross-sectional variation in the material of the first and/or second bendable longitudinal light channels around the cross-sectional circumference of the first and/or second bendable longitudinal optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; and wherein changes in the amount (e.g. power, intensity, and/or transmission loss) of light energy transmitted through the first and/or second bendable longitudinal light channels are used to measure motion (e.g. bending or rotation) of the human body joint.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there is longitudinal variation in the material and/or reflectivity of the first and/or second bendable longitudinal light channels along the longitudinal axis of the first and/or second bendable longitudinal optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there is longitudinal variation in the cross-sectional size and/or shape of the first and/or second bendable longitudinal light channels along the longitudinal axis of the first and/or second bendable longitudinal optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber);

wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the amount (e.g. power, intensity, and/or transmission loss) of light energy transmitted through the first and/or second bendable longitudinal light channels are used to measure motion (e.g. bending or rotation) of the human body joint; wherein the first and/or second bendable longitudinal light channels is made from silicone (e.g. polydimethylsiloxane or PDMS); and wherein the silicone is impregnated (e.g. doped) with light-absorbing, light-reflecting, or light-polarizing material (e.g. dye or crystals).

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there are radially asymmetric (e.g. axially-offset) connections between longitudinal segments of the first and/or second bendable longitudinal light channels or between the first and/or second bendable longitudinal light channels and adjacent longitudinal light-transmitting channels.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there is cross-sectional variation in the reflectivity and/or shape of the first and/or second bendable longitudinal light channels around the cross-sectional circumference of the first and/or second bendable longitudinal light channel (e.g. cross-sectional radial asymmetry and/or core eccentricity).

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there is cross-sectional variation in the material of the first and/or second bendable longitudinal light channels around the cross-sectional circumference of the first and/or second bendable longitudinal optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein the first and/or second bendable longitudinal light channels further comprises a Bragg grating; wherein elongation, bending, and/or twisting of the first and/or second bendable longitudinal light channels changes the spectrum of light energy transmitted through the Bragg grating in the first and/or second bendable longitudinal light channels.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there is longitudinal variation in the cross-sectional size and/or shape of the first and/or second bendable longitudinal light channels along the longitudinal axis of the first and/or second bendable longitudinal optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; wherein the first and/or second bendable longitudinal light channels further comprises a Bragg grating; and wherein elongation, bending, and/or twisting of the first and/or second bendable longitudinal light channels changes the spectrum of light energy transmitted through the Bragg grating in the first and/or second bendable longitudinal light channels.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there is longitudinal variation in the material and/or reflectivity of the first and/or second bendable longitudinal light channels along the longitudinal axis of the first and/or second bendable longitudinal optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there are radially asymmetric (e.g. axially-offset) connections between longitudinal segments of the first and/or second bendable longitudinal light channels or between the first and/or second bendable longitudinal light channels and adjacent longitudinal light-transmitting channels.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there is cross-sectional variation in the reflectivity and/or shape of the first and/or second bendable longitudinal light channels around the cross-sectional circumference of the first and/or second bendable longitudinal light channel (e.g. cross-sectional radial asymmetry and/or core eccentricity).

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; wherein changes in the spectrum of light energy caused by transmission of the light energy through the first and/or second bendable longitudinal light channels are used to measure motion (e.g. bending or rotation) of the human body joint; and wherein there is cross-sectional variation in the material of the first and/or second bendable longitudinal light channels around the cross-sectional circumference of the first and/or second bendable longitudinal optical sensor.

In an example, a wearable flexible optical sensor for measuring human motion can comprise: a first bendable longitudinal light channel through which light energy is transmitted (e.g. a bendable longitudinal optical fiber); wherein the first bendable longitudinal light channel is configured to be worn across a human body joint; wherein the first bendable longitudinal light channel is configured to span the human body joint in a longitudinal manner (e.g. the channel has a longitudinal axis which is substantially parallel to a central longitudinal axis of the body joint and/or has a substantially proximal-to-distal orientation when the body joint is maximally extended); and a second bendable longitudinal light channel through which light energy is transmitted (e.g. a bendable longitudinal optical fiber); wherein the second bendable longitudinal light channel is configured to be worn across a human body joint; wherein the second bendable longitudinal light channel is configured to span the human body joint in an oblique manner (e.g. the channel has a longitudinal axis which is oblique relative to a central longitudinal axis of the body joint) and/or helical manner; and wherein changes in the spectrum of light energy caused by transmission of the light energy through the first and/or second bendable longitudinal light channels are used to measure motion (e.g. bending or rotation) of the human body joint.

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels span the human body joint at different locations on the circumference of the body joint; wherein these different locations collectively span at least 50% of the circumference of the body joint; and wherein changes in the spectrum of light energy caused by transmission of the light energy through the plurality of bendable longitudinal light channels are used to measure motion (e.g. bending or rotation) of the human body joint.

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels comprise a multi-channel optical fiber which spans the human body joint; wherein a first bendable longitudinal light channel in the multi-channel optical fiber is a first distance from the surface of the person's body; wherein a second bendable longitudinal light channel in the multi-channel optical fiber is a second distance from the person's body; and wherein the second distance is greater than the first distance; and wherein changes in the amount (e.g. power, intensity, and/or transmission loss) of light energy transmitted through the plurality of bendable longitudinal light channels are used to measure motion (e.g. bending or rotation) of the human body joint.

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels comprise a multi-channel optical fiber which spans the human body joint; wherein a first bendable longitudinal light channel in the multi-channel optical fiber is a first distance from the surface of the person's body; wherein a second bendable longitudinal light channel in the multi-channel optical fiber is a second distance from the person's body; and wherein the second distance is greater than the first distance; and wherein changes in the spectrum of light energy caused by transmission of the light energy through the plurality of bendable longitudinal light channels are used to measure motion (e.g. bending or rotation) of the human body joint.

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels comprise a multi-channel optical fiber which spans the human body joint; wherein a first bendable longitudinal light channel in the multi-channel optical fiber is a first distance from the surface of the person's body; wherein a second bendable longitudinal light channel in the multi-channel optical fiber is a second distance from the person's body; and wherein the second distance is greater than the first distance; wherein changes in the spectrum of light energy caused by transmission of the light energy through the plurality of bendable longitudinal light channels are used to measure motion (e.g. bending or rotation) of the human body joint; wherein the plurality of bendable longitudinal light channels further comprises a Bragg grating; and wherein elongation, bending, and/or twisting of the plurality of bendable longitudinal light channels changes the spectrum of light energy transmitted through the Bragg grating in the plurality of bendable longitudinal light channels.

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels span the human body joint at different locations on the circumference of the body joint; wherein these different locations collectively span at least 50% of the circumference of the body joint; wherein changes in the spectrum of light energy caused by transmission of the light energy through the plurality of bendable longitudinal light channels are used to measure motion (e.g. bending or rotation) of the human body joint; wherein the plurality of bendable longitudinal light channels are made from silicone (e.g. polydimethylsiloxane or PDMS); and wherein the silicone is impregnated (e.g. doped) with light-absorbing, light-reflecting, or light-polarizing material (e.g. dye or crystals).

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels span the human body joint at different locations on the circumference of the body joint; wherein these different locations collectively span at least 50% of the circumference of the body joint; and wherein changes in the amount (e.g. power, intensity, and/or transmission loss) of light energy transmitted through the plurality of bendable longitudinal light channels are used to measure motion (e.g. bending or rotation) of the human body joint.

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels span the human body joint at different locations on the circumference of the body joint; wherein these different locations collectively span at least 50% of the circumference of the body joint; and wherein changes in the spectrum of light energy caused by transmission of the light energy through the plurality of bendable longitudinal light channels are used to measure motion (e.g. bending or rotation) of the human body joint.

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels span the human body joint at different locations on the circumference of the body joint; wherein these different locations collectively span at least 50% of the circumference of the body joint; and wherein changes in the amount (e.g. power, intensity, and/or transmission loss) of light energy transmitted through the plurality of bendable longitudinal light channels are used to measure motion (e.g. bending or rotation) of the human body joint.

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels span the human body joint at different locations on the circumference of the body joint; wherein these different locations collectively span at least 50% of the circumference of the body joint; wherein changes in the spectrum of light energy caused by transmission of the light energy through the plurality of bendable longitudinal light channels are used to measure motion (e.g. bending or rotation) of the human body joint; wherein the plurality of bendable longitudinal light channels further comprises a Bragg grating; and wherein elongation, bending, and/or twisting of the plurality of bendable longitudinal light channels changes the spectrum of light energy transmitted through the Bragg grating in the plurality of bendable longitudinal light channels.

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels span the human body joint at different locations on the circumference of the body joint; wherein these different locations collectively span at least 50% of the circumference of the body joint; wherein changes in the amount (e.g. power, intensity, and/or transmission loss) of light energy transmitted through the plurality of bendable longitudinal light channels are used to measure motion (e.g. bending or rotation) of the human body joint; wherein the plurality of bendable longitudinal light channels are made from silicone (e.g. polydimethylsiloxane or PDMS); and wherein the silicone is impregnated (e.g. doped) with light-absorbing, light-reflecting, or light-polarizing material (e.g. dye or crystals).

In an example, a wearable flexible optical sensor for measuring human motion can comprise: a plurality of bendable longitudinal light channels (e.g. bendable longitudinal optical fibers) through which light energy is transmitted; wherein bendable longitudinal light channels in the plurality of bendable longitudinal light channels are configured to be worn across a human body joint; wherein the bendable longitudinal light channels span the human body joint at different locations on the circumference of the body joint; wherein these different locations collectively span at least 50% of the circumference of the body joint; wherein changes in the spectrum of light energy caused by transmission of the light energy through the plurality of bendable longitudinal light channels are used to measure motion (e.g. bending or rotation) of the human body joint; wherein the plurality of bendable longitudinal light channels further comprises a Bragg grating; and wherein elongation, bending, and/or twisting of the plurality of bendable longitudinal light channels changes the spectrum of light energy transmitted through the Bragg grating in the plurality of bendable longitudinal light channels.

In an example, a wearable flexible optical sensor for measuring human motion can comprise: a bendable longitudinal light channel through which light energy is transmitted; wherein the bendable longitudinal light channel is configured to be worn across a human body joint; wherein the bendable longitudinal light channel is configured to span the human body joint in a longitudinal manner; wherein changes in light energy transmitted through the bendable longitudinal light channel are used to measure motion of the human body joint; and wherein there is longitudinal variation in the material, shape, and/or structure of the bendable longitudinal light channel along the longitudinal axis of the bendable longitudinal optical sensor.

In an example, a wearable flexible optical sensor for measuring human motion can comprise: a bendable longitudinal light channel through which light energy is transmitted; wherein the bendable longitudinal light channel is configured to be worn across a human body joint; wherein the bendable longitudinal light channel is configured to span the human body joint in a longitudinal manner; wherein changes in light energy transmitted through the bendable longitudinal light channel are used to measure motion of the human body joint; and wherein there is cross-sectional variation in the material, shape, and/or structure of the bendable longitudinal light channel around the cross-sectional circumference of the bendable longitudinal optical sensor.

In an example, a wearable flexible optical sensor for measuring human motion comprising: a bendable longitudinal light channel through which light energy is transmitted; wherein the bendable longitudinal light channel is configured to be worn across a human body joint; wherein the bendable longitudinal light channel is configured to span the human body joint in a longitudinal manner; wherein changes light energy transmitted through the bendable longitudinal light channel are used to measure motion of the human body joint; and wherein the bendable longitudinal light channel is made from polydimethylsiloxane which is impregnated and/or doped with light-absorbing, light-reflecting, or light-polarizing material.

I claim:

1. A wearable flexible optical sensor for measuring human motion comprising:
    a first bendable longitudinal light channel through which light energy is transmitted;
    wherein the first bendable longitudinal light channel is configured to be worn across a human body joint;
    wherein the first bendable longitudinal light channel has a longitudinal axis which is parallel to a central longitudinal axis of the body joint;
    wherein changes in light energy transmitted through the first bendable longitudinal light channel are used to measure motion of the human body joint; and
    wherein there is longitudinal variation in the cross-sectional size of the first bendable longitudinal light channel along the longitudinal axis of the bendable longitudinal optical sensor; and
    a second bendable longitudinal light channel through which light energy is transmitted;
    wherein the second bendable longitudinal light channel is configured to be worn across the human body joint;
    wherein the second bendable longitudinal light channel has a longitudinal axis which is oblique relative to the central longitudinal axis of the body joint;
    wherein changes in light energy transmitted through the second bendable longitudinal light channel are used to measure motion of the human body joint;
    wherein there is longitudinal variation in the cross-sectional size of the second bendable longitudinal light channel along the longitudinal axis of the bendable longitudinal optical sensor; and
    wherein the first and second bendable light channels are operatively connected together.

* * * * *